United States Patent [19]

Miyake et al.

[11] 4,394,494
[45] Jul. 19, 1983

[54] DENTAL FILLING MATERIAL

[75] Inventors: Mikio Miyake, Yamanishi; Shinya Kitoh; Satoshi Hayashi, both of Hiratsuka, all of Japan

[73] Assignee: Lion Corporation, Tokyo, Japan

[21] Appl. No.: 275,704

[22] Filed: Jun. 22, 1981

[30] Foreign Application Priority Data

Jul. 4, 1980 [JP] Japan .................................. 55-91408
Nov. 12, 1980 [JP] Japan .................................. 55-158982

[51] Int. Cl.$^3$ ...................... A61K 6/02; C08F 26/02; C07C 125/06
[52] U.S. Cl. ........................................ 526/301; 32/15; 523/105; 526/270; 526/273; 560/158
[58] Field of Search ......................... 526/301; 560/158

[56] References Cited

U.S. PATENT DOCUMENTS 3,066,112 11/1962 Bowen ................................ 523/116
4,098,918 7/1978 DeMajistre ......................... 526/301

FOREIGN PATENT DOCUMENTS 1401805 7/1975 United Kingdom .
1430303 3/1976 United Kingdom .

Primary Examiner—Harry Wong, Jr.
Attorney, Agent, or Firm—Birch, Stewart, Kolasch & Birch

[57] ABSTRACT

A dental filling material capable of forming a cured product with improved physical properties comprises a polymerizable monomer to be polymerized upon application, characterized in that the polymerizable monomer comprises a reaction product of two moles of a compound selected from the group consisting of hydroxyalkyl diacrylates and hydroxyalkyl dimethacrylates with on mole of an organic diisocyanate alone or in admixture with another polymerizable monomer. The reaction product may be bis(1,3-dimethacryloyloxy-2-propanetriyl)-N,N'-hexamethylene dicarbamate or bis(1,3-diacryloyloxy-2-propanetriyl)-N,N'-hexamethylene dicarbamate. The reaction product may be used in admixture with trimethylolpropane triacrylate and/or trimethacrylate and (mono-, di- or tri-)ethylene glycol diacrylate and/or dimethacrylate. The reaction product may also be used in admixture with bis-oxyethylenic bisphenol-A diacrylate and/or dimethacrylate and (mono-, di- or tri-)ethylene glycol diacrylate and/or dimethacrylate.

19 Claims, No Drawings

DENTAL FILLING MATERIAL

BACKGROUND OF THE INVENTION

This invention relates to a dental filling material capable of forming a cured product or filling with improved mechanical properties.

Recently, for the treatment of dental caries, composite resin has been often used as a dental filling material because it has many advantages of easy application, safety and matching color as compared with conventional filling materials such as amalgam, inlay and cement. A composite resin generally comprises monomers, polymers, inorganic fillers, catalysts or curing agents, colorants, stabilizers and the like. The composite resin usually consists of a two-paste system, one paste containing an amine catalyst, and the other paste containing a peroxide catalyst. The two pastes are formulated so as to be cured within about five minutes when a dentist mixes them. An ultraviolet-curable system is also available.

In these types of dental filling materials or composite resins, physical properties are important, including hardness, flexural strength, compressive strength, abrasion resistance, water absorption and the like. A number of filling materials have been formulated with special attention paid to physical properties, as disclosed in Bowen, U.S. Pat. No. 3,066,112, Switzerland Pat. No. 557,674, and Japanese Patent Application Laid-Open No. 48-45092. These filling materials are, however, not necessarily satisfactory in strength as compared with metallic materials. There has been a need for a dental filling material capable of forming a cured product having enhanced strength and improved physical properties.

The inventors have found that by using a monomeric reaction product of two moles of a hydroxyalkyl diacrylate or dimethacrylate with one mole of an organic diisocyanate (to be referred to as "diurethane tetraacrylate or tetramethacrylate", hereinafter) as a polymerizable monomer of a dental filling material, there is obtained a dental filling material capable of forming a cured product which not only has improved properties required for dental fillings, particularly, improved hardness, compressive strength, flexural strength and tensile strength, but also has a color tone quite similar to the tooth enamel such that substantially no aesthetic difference may be perceptible between the cured filling and the adjoining tooth enamel. This filling material is useful for actual dental treatment.

It has been known from G. B. Pat. No. 1,401,805 and G. B. Pat. No. 1,430,303 that formulating urethane diacrylate results in a cured product which is water white in color and aesthetically acceptable. However, the use of diurethane tetraacrylate or tetramethacrylate to form a cured product with improved physical properties is novel as far as the inventors know.

SUMMARY OF THE INVENTION

Accordingly, an object of the present invention is to provide a dental filling material capable of forming a cured product with improved physical properties, especially increased hardness and flexural strength.

Another object of the present invention is to provide a dental filling material capable of forming a cured product having a color tone quite similar to the tooth enamel so that substantially no difference may be perceptible between the filling and the adjoining tooth enamel.

According to one aspect of the present invention, there is provided a dental filling material comprising a polymerizable monomer to be polymerized upon application, characterized in that a reaction product of two moles of a hydroxyalkyl diacrylate and/or a hydroxyalkyl dimethacrylate with one mole of an organic diisocyanate is used as a single polymerizable monomer or in admixture with another polymerizable monomer. The reaction product is referred to diurethane tetraacrylate or tetramethacrylate.

In the dental filling material according to the present invention, a polymerizable monomer of diurethane tetraacrylate or tetramethacrylate is employed alone or in admixture with another polymerizable monomer. In the latter case, according to a preferred embodiment of the present invention, a dental filling material comprises in addition to the polymerizable monomer of diurethane tetraacrylate or tetramethacrylate, a second polymerizable monomer of trimethylolpropane triacrylate and/or trimethylolpropane trimethacrylate, and a third polymerizable monomer having the formula:

wherein R is independently a hydrogen or a methyl group, and m is equal to an integer to 1 to 3. This mixture of the monomers described above results in a cured product having further increased strength.

A cured product with further increased strength also results from a combination of diurethane tetraacrylate or tetramethacrylate, the compound having the above-mentioned formula, and a compound having the following formula:

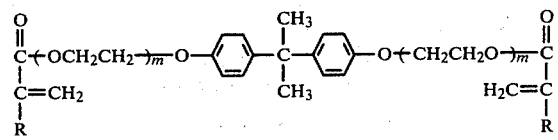

wherein R is independently a hydrogen or a methyl group and m is equal to an integer to 1 to 3.

The above and other objects, features and advantages of the present invention will become more apparent and understandable from the following descriptions.

DESCRIPTION OF THE PREFERRED EMBODIMENTS

Examples of the diurethane tetraacrylates and tetramethacrylates include those compounds having the general formula I:

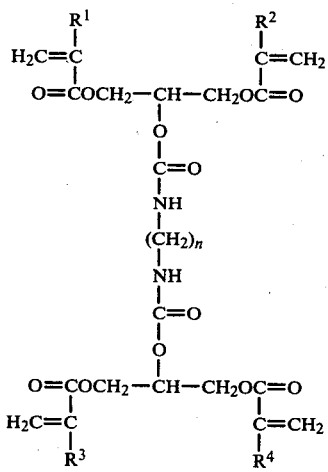

wherein $R^1$, $R^2$, $R^3$ and $R^4$ are independently hydrogens or methyl groups, and n is an integer varying from 2 to 10. The compounds of formula I are formed by reacting a reaction product of glycidyl acrylate or glycidyl methacrylate with acrylic or methacrylic acid, with an alkylene diisocyanate. Most preferred is the compound of formula I wherein $R^1$ to $R^4$ are methyl groups and n is equal to 6, that is, bis(1,3-dimethacryloyloxy-2-propanetriyl)-N,N'-hexamethylene dicarbamate. Bis(1,3-diacryloyloxy-2-propanetriyl)-N,N'-hexamethylene dicarbamate is also preferred.

The diurethane tetraacrylates and tetramethacrylates may be used either alone or in admixture of two or more. The diurethane tetraacrylate or tetramethacrylate may be used either as a single polymerizable monomer or in admixture with one or more other polymerizable monomers in the filling material of the present invention.

The other monomers which can be used in combination with the diurethane tetraacrylate and/or tetramethacrylate monomer may be mono- or polyfunctional groups. Examples of the monofunctional and polyfunctional monomers are enumerated below.

Monofunctional Monomer methyl acrylate and methacrylate,
ethyl acrylate and methacrylate,
butyl acrylate and methacrylate,
allyl acrylate and methacrylate,
hydroxyethyl acrylate and methacrylate,
methoxyethyl acrylate and methacrylate, etc.

Polyfunctional Monomer

Difunctional aliphatic acrylate and methacrylate ethylene glycol diacrylate and dimethacrylate,
diethylene glycol diacrylate and dimethacrylate,
triethylene glycol diacrylate and dimethacrylate,
polyethylene glycol diacrylate and dimethacrylate,
butylene glycol diacrylate and dimethacrylate,
neopentyl glycol diacrylate and dimethacrylate,
propylene glycol diacrylate and dimethacrylate,
1,3-butanediol diacrylate and dimethacrylate,
1,4-butanediol diacrylate and dimethacrylate,
1,6-hexanediol diacrylate and dimethacrylate, etc.

Difunctional aromatic acrylate and methacrylate 2,2-bis(acryloxyphenyl)propane,
2,2-bis(methacryloxyphenyl)propane,
2,2-bis(4-(3-acryloxy)-2-hydroxypropoxyphenyl)propane,
2,2-bis(4-(3-methacryloxy)-2-hydroxypropoxyphenyl)propane,
2,2-bis(4-acryloxyethoxyphenyl)propane,
2,2-bis(4-methacryloxyethoxyphenyl)propane,
2,2-bis(4-acryloxydiethoxyphenyl)propane,
2,2-bis(4-methacryloxydiethoxyphenyl)propane,
2,2-bis(4-acryloxytriethoxyphenyl)propane,
2,2-bis(4-methacryloxytriethoxyphenyl)propane,
2,2-bis(4-acryloxytetraethoxyphenyl)propane,
2,2-bis(4-methacryloxytetraethoxyphenyl)propane,
2,2-bis(4-acryloxypentaethoxyphenyl)propane,
2,2-bis(4-methacryloxypentaethoxyphenyl)propane,
2,2-bis(4-acryloxybutoxyphenyl)propane,
2,2-bis(4-methacryloxybutoxyphenyl)propane,
2,2-bis(4-acryloxydibutoxyphenyl)propane,
2,2-bis(4-methacryloxydibutoxyphenyl)propane,
2,2-bis(4-acryloxydipropoxyphenyl)propane,
2,2-bis(4-methacryloxydipropoxyphenyl)propane,
2,2-bis(4-acryloxytripropoxyphenyl)propane,
2,2-bis(4-methacryloxytripropoxyphenyl)propane,
2-(4-acryloxyethoxyphenyl)-2-(4-acryloxydiethoxyphenyl)propane,
2-(4-methacryloxyethoxyphenyl)-2-(4-methacryloxydiethoxyphenyl)propane,
2-(4-acryloxydiethoxyphenyl)-2-(4-acryloxytriethoxyphenyl)propane,
2-(4-methacryloxydiethoxyphenyl)-2-(4-methacryloxytriethoxyphenyl)propane,
2-(4-acryloxydipropoxyphenyl)-2-(4-acryloxytriethoxyphenyl)propane,
2-(4-methacryloxydipropoxyphenyl)-2-(4-methacryloxytriethoxyphenyl)propane,
2,2-bis(4-acryloxypropoxyphenyl)propane,
2,2-bis(4-methacryloxypropoxyphenyl)propane,
2,2-bis(4-acryloxyisopropoxyphenyl)propane,
2,2-bis(4-methoacryloxyisopropoxyphenyl)propane,
xylylene glycol diacrylate,
xylylene glycol dimethacrylate, etc.

Trifunctional aliphatic acrylate and methacrylate trimethylolpropane triacrylate and trimethacrylate,
trimethylolethane triacrylate and trimethacrylate,
trimethylolethanol triacrylate and trimethacrylate,
trimethylolmethane triacrylate and trimethacrylate,
pentaerythritol triacrylate and trimethacrylate, etc.

Tetrafunctional acrylate and methacrylate tetramethylolmethane tetraacrylate and tetramethacrylate, etc.

When the diurethane tetraacrylate or tetramethacrylate monomer is used in admixture with other monomers, the former may be blended in an amount of 5–80% by weight, preferably 5–60% by weight, more preferably 10–60% by weight of the total weight of the polymerizable monomers.

Among these additional polymerizable monomers, most preferred is a combination of trimethylolpropane triacrylate and/or trimethacrylate and a monomeric compound of the general formula II:

wherein R is a hydrogen or a methyl group, and m is an integer of 1 to 3. The strength of a cured product is further increased by using the diurethane tetraacrylate and/or tetramethacrylate in admixture with this combination of trimethylolpropane triacrylate and/or trimethacrylate and a monomeric compound of formula II. Preferred examples of the compound of formula II are mono-, di- and tri-ethylene glycol diacrylate and dimethacrylate, particularly, triethylene glycol diacrylate and triethylene glycol dimethacrylate.

When the three types of monomers are used together, that is, when the diurethane tetraacrylate and/or tetramethacrylate is used in admixture with the trimethylol propane triacrylate and/or trimethacrylate and the compound of formula II, the trimethylolpropane triacrylate and/or trimethacrylate may be blended in an amount of 10–60%, more preferably 15–50% by weight and the compound of formula II may be blended in an amount of 10–60%, more preferably 15–50% by weight of the total weight of the polymerizable monomers. Within these blending ranges, the diurethane tetraacrylate and tetramethacrylate will most effectively function. As described above, the diurethane tetraacrylate and/or tetramethacrylate may preferably be blended in an amount of 5–80%, especially 10–60% by weight of the total weight of the polymerizable monomers because increased blending amounts will increase the viscosity of a monomer mixture and result in a cured product having increased water absorption.

According to a further aspect of the present invention, a cured product having improved physical properties can be obtained by using the diurethane tetraacrylate and/or tetramethacrylate in admixture with one or more monomeric compounds of the formula II and one or more monomeric compounds selected from bis-oxyethylenic bisphenol-A diacrylates and dimethacrylates having the general formula III:

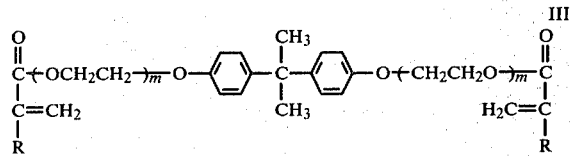

wherein R is a hydrogen or a methyl group, and m is an integer of 1 to 3. In this case, the diurethane tetraacrylate and/or tetramethacrylate may preferably be blended in an amount of 5–80%, especially 10–60% by weight of the polymerizable monomers. The compound of formula II may be blended in an amount of 10–60% by weight and the compound of formula III may be blended in an amount of 10–80%, more preferably 10–60% by weight of the polymerizable monomers.

It is also contemplated in the present invention that additional oligomers and polymers may be blended in an amount of 0–30% by weight of the polymerizable monomers with the above-mentioned monomers for the purpose of regulating viscosity, curing rate and curing shrinkage, for example, methyl acrylate, methyl methacrylate, hydroxyethyl acrylate, hydroxyethyl methacrylate, tetrahydrofurfuryl acrylate, tetrahydrofurfuryl methacrylate, glycidyl acrylate, glycidyl methacrylate, styrene, and the like.

Also included are fillers which serve to increase the compressive strength, hardness and other physical properties of a cured product. Inorganic fillers are usually employed although organic fillers may be employed to improve surface gloss of a cured product and the affinity or bonding with polymerizable monomers. The inorganic fillers include alpha-quartz, fumed silica, glass beads, aluminum oxide, and the like. The particle size is not particularly limited although fillers having a particle size of less than 100 microns, especially less than 50 microns are preferred. Those fillers having a particle size as small as several microns or less are also preferred to increase surface smoothness. Also included is a combination of particles having a size of several ten microns and particles having a size of several microns. The inorganic fillers may preferably be pretreated with a silane coupling agent in order to obtain an improved bonding with monomers. Examples of the silane coupling agent for such pretreatment are vinyl trichlorosilane, vinyl triethoxysilane, vinyl trimethoxysilane, vinyl tris($\beta$-methoxyethoxy)silane, $\gamma$-methacryloxypropyl trimethoxysilane, N-($\beta$-aminoethyl)$\gamma$-aminopropyl trimethoxysilane, and the like. The organic fillers which can be employed herein are those prepared by finely dividing a polymer of any of the above-mentioned monomers to a particle size of less than 50 microns in a ball mill or any suitable means. Another procedure to prepare organic fillers is polymerization of monomers dispersing inorganic fillers having a particle size of less than 10 microns. The polymerization cured product is finely divided to a particle size of less than 50 microns in a ball mill or any suitable means. It is to be noted that the filler may be blended in an amount of 50–80% by weight of the total weight of a filling material.

A catalyst or curing agent may be blended in the filling material according to the present invention. Any suitable known catalyst or curing agent may be used, for example, a combination of an amine and a peroxide, or sulfinic acid or its derivatives and a peroxide. When such a combination of curing agents is used, the above-mentioned necessary monomer or monomers and optional additives may be divided into two groups or a composition comprising the necessary monomer(s) and optional additives may be divided into two portions such that the amine or sulfinic acid derivative may be blended into one while the peroxide may be blended into the other. Immediately before application, these two portions are blended into a mixture which will cure naturally. The amine may include N,N-dimethyl-p-toluidine, N,N'-di($\beta$-hydroxyethyl)-p-toluidine, N,N-dimethyl aniline, monoethanol amine and the like. The content of the amine may preferably be in the range of from 0.1 to 5% by weight of the polymerizable monomers. Derivatives of sulfinic acid may be benzene sulfinic acid, p-toluene sulfinic acid and their sodium salts, and the like. The content of sulfinic acid or its derivatives may preferably be in the range of from 2 to 6% by weight of the polymerizable monomers. The peroxide may include benzoyl peroxide, di-p-chloro-benzoyl peroxide, di-lauroyl-peroxide, methyl ethyl ketone peroxide and the like. The content of the peroxide may preferably be in the range of from 0.1 to 3% by weight of the polymerizable monomers.

The composition may also be formulated into an ultraviolet curable system by blending an ultraviolet sensitizer such as benzoin methyl ether, acetophenone, benzophenone, 2,2,2-trichloro-4'-t-buthylacetophenone, anthraquinone and the like in an amount of 0.3–3% by weight of the monomers. In this case, all the necessary ingredients may be blended into a single composition which must be packed in a UV-shielded package.

In addition, a polymerization inhibitor, colorant, antioxidant and other additives may be blended in the filling material according to the present invention, if desired. Optionally, hydrocarbons such as paraffin, liquid paraffin, anhydrous vaseline, microcrystalline wax, squalane, etc.; waxes such as lanolin, liquid lanolin, beeswax, etc.; organic acid esters such as isopropyl myristate, myristyl myristate, isopropyl palmitate, etc., and other oily substances may be blended in an amount of 0 to 10%, especially 0.1 to 10% by weight of the monomers. The resulting cured product has further improved abrasion resistance.

The present invention will be more fully understood by referring to the following examples and comparative examples. However, the following examples are not to be construed to limit the scope of the invention. In these examples, parts are all by weight.

EXAMPLE 1 AND COMPARATIVE EXAMPLE 1

Dental filling materials were prepared according to the following formulations A and B.

Formulation A (Comparison)

To 100 parts of a mixture of polymerizable monomers, 2,2-bis(4-acryloxydiethoxyphenyl)propane and triethylene glycol dimethacrylate at a weight ratio of 2:3 was added 257 parts of α-quartz treated with γ-methacryloxypropyl trimethoxysilane. The resulting mixture was divided into two portions. One part of benzoyl peroxide was added to one portion while one part of N,N-dimethyl-p-toluidine was added to the other portion.

Equal amounts of these two portions were admixed to form a cured sample.

Formulation B (Invention)

A cured sample was obtained by repeating the procedure described for formulation A except that the polymerizable monomer mixture was a mixture of 2,2-bis(4-acryloxydiethoxyphenyl)propane, triethylene glycol dimethacrylate, and the compound of formula I wherein $R^1$ to $R^4$ are $CH_3$ and n is equal to 6, that is, bis(1,3-dimethacryloyloxy-2-propanetriyl)-N,N'-hexamethylene dicarbamate at a weight ratio of 2:3:1.

The cured samples were determined for Barcol hardness, compressive strength, diametral tensile strength, and flexural strength according to the following methods. The results are shown in Table 1.

Hardness

A cured sample was immersed in distilled water at a temperature of 37° C. for 24 hours before the hardness of the sample was measured using the Barcol hardness tester model No. GYZJ 934-1.

Compressive strength

A cured disc sample having a diameter of 6 mm and a height of 3 mm was formed and immersed in distilled water at a temperature of 37° C. for 24 hours before a compression test was carried out at a compression rate of 10 mm/min. using the Strograph-U.

Diametral tensile strength

A cured disc sample having a diameter of 6 mm and a height of 3 mm was formed and immersed in distilled water at a temperature of 37° C. for 24 hours. The sample disc was placed on its side between parallel platens of the testing machine, the Strograph-U. A small piece of blotting paper wet with water was inserted between the platens of the machine and each side of the sample disc. The sample was loaded continuously in compression at 10 mm/min. to the breaking point.

Flexural strength

A cured sample having a width of 2 mm, a length of 25 mm and a thickness of 2 mm was formed according to ISO 4049. The sample was immersed in distilled water at a temperature of 37° C. for 24 hours before flexural strength test was carried out at a rate of 1 mm/min. on the Strograph-U.

TABLE I

|  | A(comparison) | B(invention) |
|---|---|---|
| Hardness, Barcol | 65 | 73 |
| Compressive strength, kg/cm² | 2551 | 3611 |
| Diametral tensile strength, MN/m² | 36 | 55 |
| Flexural strength, kg/cm² | 988 | 1104 |

EXAMPLE 2

To 100 parts of a mixture of polymerizable monomers, bis(1,3-dimethacryloyloxy-2-propanetriyl)-N,N'-hexamethylene dicarbamate, triethylene glycol dimethacrylate, and trimethylolpropane trimethacrylate at a weight ratio of 2:3:1 was added 257 parts of α-quartz treated with γ-methacryloxypropyl trimethoxysilane. After thorough mixing, the mixture was divided into two portions. One part of benzoyl peroxide was added to one portion while one part of N,N-dimethyl-p-toluidine was added to the other portion.

Equal amounts of these two portions were thoroughly admixed to obtain a cured sample. The physical properties of the sample were determined as described in Example 1. The results are shown in Table II.

TABLE II

| Hardness, Barcol | 80 |
|---|---|
| Compressive strength, kg/cm² | 3472 |
| Diametral tensile strength, MN/m² | 52 |
| Flexural strength, kg/cm² | 1303 |

EXAMPLE 3

To 100 parts of a mixture of polymerizable monomers, bis(1,3-dimethacryloyloxy-2-propanetriyl)-N,N'-hexamethylene dicarbamate and trimethylolpropane trimethacrylate at a weight ratio of 3:2 was added 257 parts of α-quartz treated with γ-methacryloxypropyl trimethoxysilane. After thorough mixing, the mixture was divided into two portions. One part of benzoyl peroxide was added to one portion while one part of N,N'-di(β-hydroxyethyl)-p-toluidine was added to the other portion.

Equal amounts of these two portions were thoroughly admixed to obtain a cured sample. The physical properties of the sample were determined as descried in Example 1. The results are shown in Table III.

TABLE III

| Hardness, Barcol | 79 |
|---|---|
| Compressive strength, kg/cm² | 3155 |
| Diametral tensile strength, MN/m² | 42 |

TABLE III-continued

| | |
|---|---|
| Flexural strength, kg/cm$^2$ | 1261 |

EXAMPLE 4

To 100 parts of a mixture of polymerizable monomers, bis(1,3-dimethacryloyloxy-2-propanetriyl)-N,N'-hexamethylene dicarbamate, triethylene glycol dimethacrylate, and methyl methacrylate at a weight ratio of 2:3:½, 10 parts of poly(methyl methacrylate) having a degree of polymerization of 7,000–7,500 was dissolved and 250 parts of α-quartz treated with γ-methacryloxypropyl trimethoxysilane was added. After thorough mixing, the mixture was divided into two portions. One part of benzoyl peroxide was added to one portion while one part of N,N-di(β-hydroxyethyl)-p-toluidine was added to the other portion.

Equal amounts of these two portions were thoroughly admixed to obtain a cured sample. The physical properties of the sample were determined as described in Example 1. The results are shown in Table IV.

TABLE IV

| | |
|---|---|
| Hardness, Barcol | 72 |
| Compressive strength, kg/cm$^2$ | 3138 |
| Diametral tensile strength, | 58 |
| Flexural strength, kg/cm$^2$ | 1258 |

EXAMPLES 5 AND 6 AND COMPARATIVE EXAMPLE 2

Dental filling materials were prepared according to the following formulations C, D and E.

Formulation C (Invention)

To 100 parts of each of mixtures of polymerizable monomers, bis(1,3-dimethacryloyloxy-2-propanetriyl)-N,N'-hexamethylene dicarbamate and trimethyloylpropane trimethacrylate at weight ratios of 4:1 (sample C-a), 3:2 (sample C-b), 2:3 (sample C-c) and 1:4 (sample C-d), respectively, was added 257 parts of α-quartz treated with γ-methacryloylpropyl trimethoxysilane. The resulting mixture was divided into two portions. One part of benzoyl peroxide was added to one portion while one part of N,N-dimethyl-p-toluidine was added to the other portion.

Equal amounts of these two portions were admixed to obtain a cured sample.

Formulation D (Comparison)

A cured sample was obtained by the same procedure described for formulation C except that the polymerizable monomer mixture was a mixture of 2,2-bis(4-acryloxydiethoxyphenyl)propane, triethylene glycol dimethacrylate, and trimethylolpropane trimethacrylate at a weight ratio of 2:3:1.

Formulation E (Invention)

To 100 parts of a mixture of polymerizable monomers, bis(1,3-dimethacryloyloxy-2-propanetriyl)-N,N'-hexamethylene dicarbamate, trimethylolpropane trimethacrylate, and triethylene glycol dimethacrylate at a weight ratio of 2:3:1 was added 257 parts of α-quartz treated with γ-methacryloxypropyl trimethoxysilane. After thorough mixing, the mixture was divided into two portions. One part of benzoyl peroxide was added to one portion while one part of N,N-dimethyl-p-toluidine was added to the other portion.

Equal amounts of these two portions were admixed to obtain a cured sample.

The cured samples were determined for Barcol hardness, compressive strength, diametral tensile strength, and flexural strength according to the methods as described in Example 1. The results are shown in Table V.

TABLE V

| Example | Hardness, Barcol | Compressive strength, kg/cm$^2$ | Diametral tensile strength MN/m$^2$ | Flexural strength, kg/cm$^2$ |
|---|---|---|---|---|
| C-a | 79 | 2750 | 42 | 1165 |
| C-b | 79 | 3155 | 42 | 1260 |
| C-c | 80 | 2980 | 43 | 1100 |
| C-d | 78 | 2950 | 39 | 900 |
| D | 75 | 3395 | 50 | 990 |
| E | 82 | 3600 | 52 | 1410 |

It was found that similar results were obtained when the diurethane tetraacrylate of formula I wherein $R^1$–$R^4$ are hydrogens and n is equal to 6 was used.

EXAMPLE 7

To 100 parts of a mixture of polymerizable monomers, bis(1,3-dimethacryloyloxy-2-propanetriyl)-N,N'-hexamethylene dicarbamate, trimethylolpropane trimethacrylate, and triethylene glycol dimethacrylate at a weight ratio of 3:2:1 was added 280 parts of α-quartz treated with γ-methacryloxypropyl trimethoxysilane. After thorough mixing, the mixture was divided into two portions. One and a half parts of benzoyl peroxide were added to one portion while 1.5 parts of N,N-dimethyl-p-toluidine were added to the other portion.

Equal amounts of these two portions were thoroughly admixed to obtain a cured sample. The physical properties of the sample were determined as described in Example 1. The results are shown in Table VI.

TABLE VI

| | |
|---|---|
| Hardness, Barcol | 82 |
| Compressive strength, kg/cm$^2$ | 3830 |
| Diametral tensile strength, MN/m$^2$ | 58 |
| Flexural strength, kg/cm$^2$ | 1350 |

EXAMPLE 8

To 100 parts of a mixture of polymerizable monomers, bis(1,3-dimethacryloyloxy-2-propanetriyl)-N,N'-hexamethylene dicarbamate, trimethylolpropane trimethacrylate, and triethylene glycol dimethacrylate at a weight ratio of 1:2:3 was added 280 parts of α-quartz treated with γ-methacryloxypropyl trimethoxysilane. After thorough mixing, the mixture was divided into two portions. One and a half parts of benzoyl peroxide were added to one portion while 1.5 parts of N,N-di(β-hydroxyethyl)-p-toluidine were added to the other portion.

Equal amounts of these two portions were thoroughly admixed to obtain a cured sample. The physical properties of the sample were determined as described in Example 1. The results are shown in Table VII.

TABLE VII

| | |
|---|---|
| Hardness, Barcol | 81 |
| Compressive strength, kg/cm$^2$ | 3525 |
| Diametral tensile strength, MN/m$^2$ | 52 |

What is claimed is:

1. A polymerizable monomer having the formula:

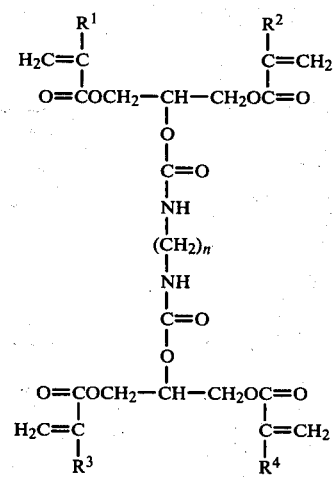

wherein $R^1$, $R^2$, $R^3$ and $R^4$ are each hydrogen or a methyl group and n is equal to a value varying from 2 to 10.

2. A dental filling composition, comprising: a polymerizable monomer having the formula I:

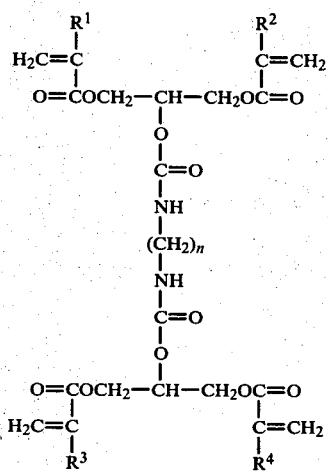

wherein $R^1$, $R^2$, $R^3$ and $R^4$ are each a hydrogen or a methyl group and n is equal to a value varying from 2 to 10 and a filler material.

3. A dental filling composition according to claim 2, wherein said monomer of formula I is bis(1,3-dimethacryloyl-oxy-2-propanetriyl)-N,N'-hexamethylene dicarbamate.

4. A dental filling composition according to claim 2, wherein said monomer of formula I is bis(1,3-diacryloyloxy-2-propanetriyl)-N,N'-hexamethylene dicarbamate.

5. A dental filling composition according to claim 2, and further including at least one other polymerizable monomer.

6. A dental filling composition according to claim 2, wherein said monomer of formula I is present in admixture with another polymerizable monomer, said monomer of formula I being present in an amount of 5 to 80% by weight of the total weight of the polymerizable monomers.

7. A dental filling composition according to claim 6, wherein said monomer of formula I is present in an amount of 10 to 60% by weight of the total weight of the polymerizable monomers.

8. A dental filling composition according to claim 2, wherein said monomer of formula I is present in admixture with a polymerizable monomer selected from the group consisting of trimethylolpropane triacrylate, trimethylolpropane trimethacrylate and mixtures thereof, and a polymerizable monomer having the general formula II:

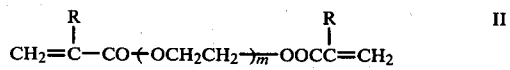

wherein R is a hydrogen or a methyl group, and m is equal to a value varying from 1 to 3.

9. A dental filling composition according to claim 8, wherein said monomer of formula II is selected from the group consisting of triethylene glycol diacrylate, triethylene glycol dimethacrylate and a mixture thereof.

10. A dental filling composition according to claim 8, wherein said monomer of formula I is present in an amount of 5 to 80% by weight of the total weight of the polymerizable monomers, said monomer selected from the group consisting of trimethylolpropane triacrylate, trimethylolpropane trimethacrylate and a mixture thereof is present in an amount of 10–60% by weight of the total weight of the polymerizable monomers, and said monomer of formula II is present in an amount of 10–60% by weight of the total weight of the polymerizable monomers.

11. A dental filling composition according to claim 10, wherein said monomer of formula I is present in an amount of 10 to 60% by weight of the total weight of the polymerizable monomers, said monomer selected from the group consisting of trimethylolpropane triacrylate, trimethylolpropane trimethacrylate and a mixture thereof is present in a amount of 15–50% by weight of the total weight of the polymerizable monomers, and said monomer of formula II is present in an amount of 15–50% by weight of the total weight of the polymerizable monomers.

12. A dental filling composition according to claim 2, wherein said monomer of formula I is present in admixture with a polymerizable monomer having the general formula II:

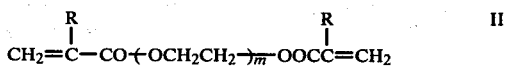

wherein R is a hydrogen or a methyl group, and m is equal to a value varying from 1 to 3, and a polymerizable monomer having the general formula III:

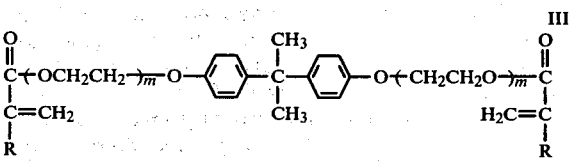

wherein R is a hydrogen or a methyl group, and m is equal to a value varying from 1 to 3.

13. A dental filling composition according to claim 12, wherein said monomer of formula I is bis(1,3-dimethacryloyl-oxy-2-propanetriyl)-N,N'-hexamethylene dicarbamate.

14. A dental filling composition according to claim 12, wherein said monomer of formula I is bis(1,3-diacryloyloxy-2-propanetriyl)-N,N'-hexamethylene dicarbamate.

15. A dental filling composition according to claim 12, wherein said monomer of formula II is selected from the group consisting of triethylene glycol diacrylate, triethylene glycol dimethacrylate and a mixture thereof.

16. A dental filling composition according to claim 12, wherein said monomer of formula I is present in an amount of 5 to 80% by weight of the total weight of the polymerizable monomers, said monomer of formula II is present in an amount of 10–60% by weight of the total weight of the polymerizable monomers, and said monomer of formula III is present in an amount of 10–80% by weight of the polymerizable monomers.

17. A dental filling composition according to claim 16, wherein said monomer of formula I is present in an amount of 10 to 60% by weight of the total weight of the polymerizable monomers, said monomer of formula II is present in an amount of 10–60% by weight of the total weight of the polymerizable monomers, and said monomer of formula III is present in an amount of 10–60% by weight of the total weight of the polymerizable monomers.

18. A dental filling composition, comprising: a polymerizable monomer having the formula I:

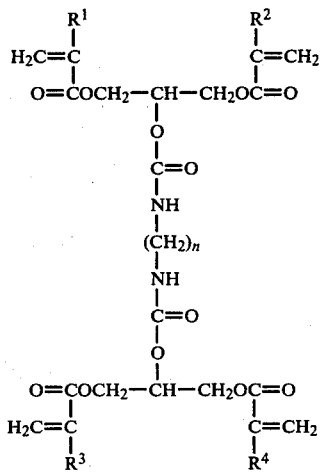

wherein $R^1$, $R^2$, $R^3$ and $R^4$ are each a hydrogen or a methyl group, and n is equal to a value varying from 2 to 10; at least one other polymerizable monomer; a filler; and a catalyst.

19. A dental filling composition according to claim 18, wherein said polymerizable monomer I is present in an amount of 5 to 80% by weight of the total weight of the polymerizable monomers.

* * * * *